United States Patent [19]

Kopman

[11] 4,402,683
[45] Sep. 6, 1983

[54] CANNULA INTRODUCER

[76] Inventor: Ercument A. Kopman, 9814 Greenery La., Olivette, Mo. 63132

[21] Appl. No.: 335,243

[22] Filed: Dec. 28, 1981

[51] Int. Cl.³ .......................................... A61M 25/02
[52] U.S. Cl. .................................. 604/175; 128/325; 128/DIG. 26
[58] Field of Search ................... 128/348, 349 R, 350, 128/214 R, 334 C, 325, DIG. 26, 335; 604/28, 49, 53, 175

[56] References Cited

U.S. PATENT DOCUMENTS

| | | | |
|---|---|---|---|
| 2,792,003 | 5/1957 | Cantor | 604/275 X |
| 3,683,911 | 8/1972 | McCormick | 128/214 R |
| 4,016,884 | 4/1977 | Kwan-Gett | 128/348 |
| 4,129,129 | 12/1978 | Amrine | 604/49 |
| 4,184,497 | 1/1980 | Kolff et al. | 128/348 |
| 4,248,224 | 2/1981 | Jones | 128/348 X |
| 4,301,797 | 11/1981 | Pollack | 604/4 |
| 4,306,545 | 12/1981 | Ivan et al. | 128/334 C X |
| 4,309,994 | 1/1982 | Grunwald | 128/348 X |
| 4,318,401 | 3/1982 | Zimmerman | 604/53 X |

Primary Examiner—Richard J. Apley
Assistant Examiner—Michelle N. Lester
Attorney, Agent, or Firm—Paul M. Denk

[57] ABSTRACT

A cannula introducer for use in open heart surgery and provided for locating through an incision in the heart lining, the introducer includes a cylindrical member, formed at its upper end into a pair of tubular-like guide means, while its lower end is formed into confinement, having a pair of apertures therethrough, and through which the cannula are directed for insertion into the vena cava during the application of a heart-lung machine during a surgical procedure, and through which the cannulas may be introduced and guided into the heart, and more specifically its right atrium, and further into the superior and inferior vena cavae in preparation and during open heart and related type surgical operations, requiring the application of two separate cannulas, at the mid-point of the introducer may be located an integral beaded portion therearound, to facilitate the adherence and tying of the wall of the right atrium to the introducer while it is located within the same during a surgical procedure.

4 Claims, 5 Drawing Figures

CANNULA INTRODUCER

CROSS REFERENCE TO RELATED APPLICATION

The subject matter of this application is related to the subject matter set forth in the disclosure document of Ercumen A. Kopman filed in the U.S. Patent and Trademark Office on Dec. 9, 1980, and granted disclosure document Ser. No. 096,195.

BACKGROUND OF THE INVENTION

This invention relates generally to a cannula introducer, and one that may be adhered to an aperture provided within the wall of the heart, and more particularly its right atrium or auricle, as for use in preparation for open heart surgery.

During open heart surgery, or in preparation for the same, it is essential to introduce when is generally defined as a heart-lung machine into the operations of the heart in order that the blood supply of the patient being operated upon can continue to flow within the body even during performance of the operational procedure. Normally, a pair of cannulas are introduced into the structure of the heart, usually at the vicinity of its right atrium, with one cannula extending upwardly into the superior vena cava, while the second cannula extend downwardly into the inferior vena cave, and thereby continue to supply and pump blood throughout all parts of the body during performance of the surgical operation. The cannulas when emplaced through the heart wall in the aforesaid manner, and which is commonly performed in practice, is simply located through one but usually two apertures made through the lining of the heart, and then tied in place by means of a ligature in order for said cannulas to remain in place and continue to divert venous blood to the heart lung machine, during the cardiopulmonary bypass surgery. One problem is frequently encountered during usage of the foregoing process, which is common in practice, and that is that frequently leakage of blood will occur at the location where the pair of cannulas extend through the incision made into the right atrium. This is normally because the pair of cannulas that are maintained in adjacency undertake the configuration of a figure eight, in cross-section, making it difficult to tie the heart lining or wall into a close confining relationship entirely around the proximate cannula, meaning that some leakage does occur as a result of the imperfect contact maintained between the heart lining and the contiguous pair of cannula.

It is, therefore, the principal object of this invention to eliminate the second hole or incision that normally is placed into the wall of the atrium during open heart surgery and which is difficult to reach and repair at the conclusion of a cardiopulmonary bypass operation.

Another main reason for this invention is to eliminate one potential bleeding side in the wall of the atrium during and after open heart surgery generally through the procedure that necessitates only the forming of one incision therein to accommodate the mechanical mechanism utilized during open heart surgery.

A third principal reason for this invention is to give the surgeon the opportunity to use two cannulas through one incision during the surgical procedure requiring two sets of cannulas, such as intracardiae repair and valve replacement operations, and which advantage is attained through the usage of the introducer of this invention.

Another object of this invention is to provide a cannula introducer that has a confined inward end, or that end that extends into the heart cavity, and more specifically the right auricle, and which confined end has a pair of apertures located therein and properly oriented so that as the cannula are introduced into the interior of the atrium, they will be conveniently directed towards the location of the various vena cava in which each of the cannula is intended to locate during operation of the heart-lung machine.

Another object of this invention is to provide a beaded approximate mid-point for the cylindrical member forming the cannula introducer, so as to facilitate the tying of the lining of the heart by means of a ligature to the introducer in preparation for the insertion of the cannula therein during performance of the identified surgical operation.

Another object of this invention is the provision of guide means integrally of the introducer for directing the cannula properly into and through the invention during its usage.

These and other objects will become more apparent to those skilled in the art upon reviewing the summary of this invention, and upon undertaking a study of the description of the preferred embodiment in view of the drawings.

SUMMARY OF THE INVENTION

This invention, as reviewed herein, relates to an improved means for introducing cannulae into the various cavities of the heart, in preparation for and during the performance of open heart surgery. Heretofore the various cannulae introduced during open heart surgery would generally be introduced into the right atrium, or auricle as it is otherwise known, as aforesaid, through a series of holes punctured into the wall of the atrium, and which would be tied in place as previously identified in the background of this invention.

Generally there are two cannulae involved, one is located up into the superior vena cava, with the other cannula being inserted down into the inferior vena cava that opens into the right auricle or atrium of the heart. As is known, blood is returning from the body extremities through the vena cavae and return the impurities and carbon dioxide laden blood back into the heart, in preparation for its pumping back out into the area of the lungs, where such impurities are removed and fresh oxygen is replenished into the blood stream.

In view of the foregoing, the concept of puncturing a number of holes into the atrium liner of the heart is undesirable, since, as previously explained, bleeding frequently does occur, and particularly after the operation is completed, there is a necessity for two such punctures to be sewn up, and heal under the natural processes of the body. The current invention, on the other hand, is designed incorporating a bifurcated type of cannula supporting means, or introducer as identified herein, and this introducer means comprises a cylindrical member or tube-like means that includes guides at one end, while its lower, confining or closing end incorporates a pair of apertures, that is useful for directing a pair of cannula into the superior and inferior vena cavae, as identified. The upper or guide forming end of the cylindrical means may include a beaded rim, integrally formed therein, which facilitates the adherence of the introducer through a single opening made through the right atrial appendix, and its tying in place by means of a ligature, as shown. Thus, the introduction and retention of the introducer means within the heart is attained through the incision of a single puncture within the atrium wall, and which puncture may be circular in shape and quite similar to the cross-sectional dimension of the introducer itself. Thus, leakage of blood is effectively minimized and eliminated through the use of the shaped introducer means of this invention.

The bottom or confining end of the introducer, as previously explained, includes a pair of apertures which function to receive and accept the introduction of individual cannula therethrough, and at the same time the said apertures are properly aligned for conveniently directing each cannula into its respective vena cava.

The two plastic cannulae generally used in the prior art during open heart surgery are located within the heart, in the manner as previously described, with the introducer means of this invention likewise being formed of a polymer or plastic, or even of rubber, and which can be immediately discarded after completion of the open heart surgery. The introducer means of this invention necessitates only a single opening through the heart liner, during its application, and once the introducer means is removed, a single line of sutures are simply required for closing off the puncture, and which can easily and effectively prevent any further bleeding which normally occurs where a pair of such punctures were usually required and located during the prior art and current day heart-lung machine type of open heart surgery. Control of bleeding under the prior art type of surgical procedure is quite difficult, but such has been significantly alleviated and reduced through the usage of the current invention.

DESCRIPTION OF THE PREFERRED EMBODIMENT

Figure 1:
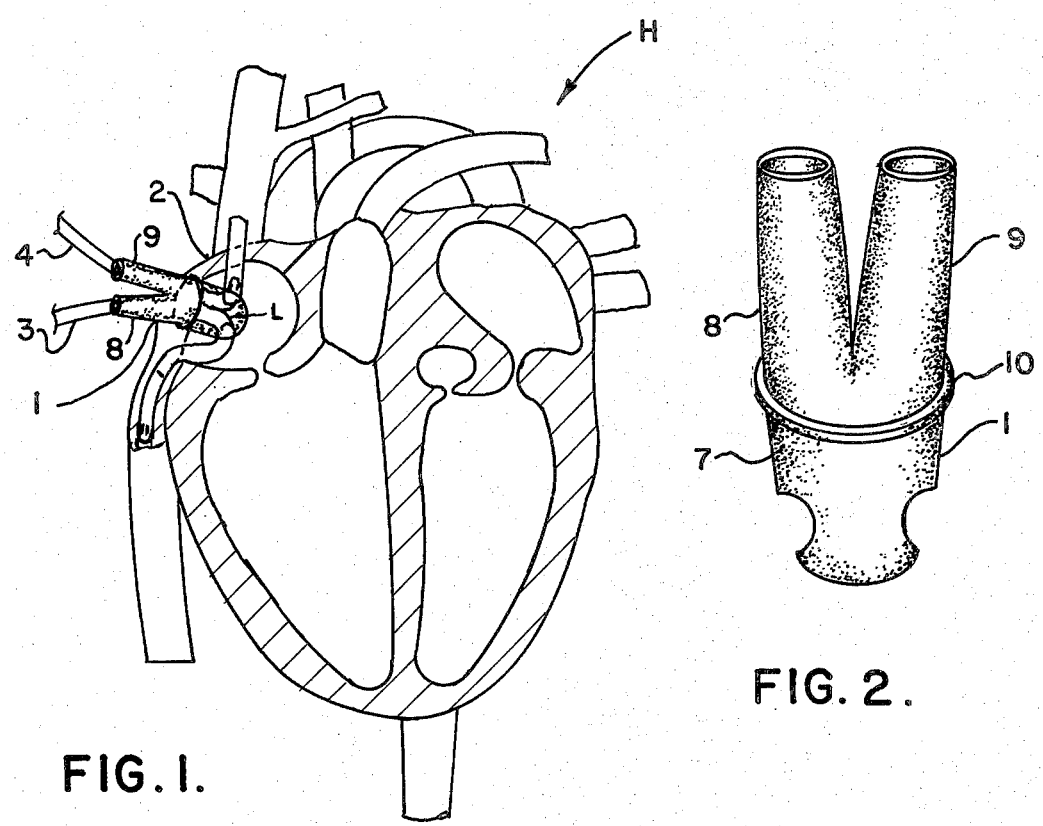
FIG. 1 discloses a perspective view of the human heart with the cannula introducer and the pair of cannulae located therein in preparation and during the performance of an open heart surgery operation.
Figure 2:
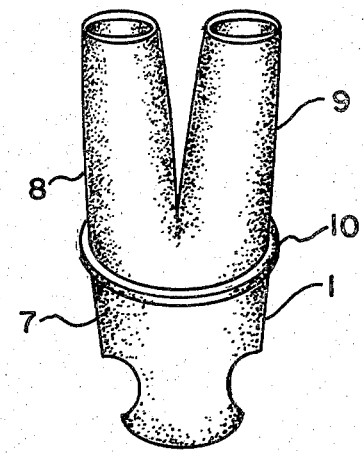
FIG. 2 provides an isometric view of the cannula introducer of this invention.
Figure 3:
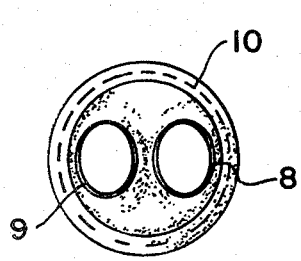
FIG. 3 provides a top view of the cannula introducer as disclosed in FIG. 2.
Figure 4:
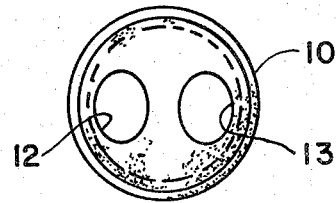
FIG. 4 provides a bottom view of the cannula introducer of this invention.
Figure 5:
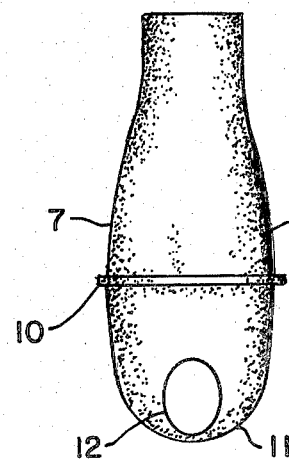
FIG. 5 provides a side view of the cannula introducer of this invention.

In referring to the drawings, and in particular FIG. 1, there is disclosed the human heart H having the cannula introducer 1 located through a single puncture or incision made generally through the right atrial appendix, as at 2, of the structure of the heart. As can further be seen from FIG. 1, a pair of cannulae 3 and 4 have been located through the introducer means, with the cannula 3 extending downwardly into the inferior vena cava 5 of the heart, while the second cannula 4 extends upwardly into the superior vena cava 6, so that during operations of the heart lung machine, blood supply can flow between the vena cava and maintain the flow of blood through the body even during the performance of the surgical procedure.

As can be seen in FIGS. 2 through 5, the introducer means 1 is generally of a cylindrical shape, as shown at 7, having an upper forming a pair of guide means 8 and 9, and also formed having a beaded edge as at 10 located therearound and which facilitates the tying by means of a ligature of the heart lining to the introducer during its insertion and locating within the wall of the heart in preparation and during the operation. The bottom or lower end of the cylindrical member 7 is generally confined towards closure, as at 11, and contains a pair of apertures, as at 12 and 13, therethrough, and through which the various cannulae 3 and 4 locate and insert in preparation and during surgery. Generally these apertures 11 and 12 are located at vicinities that provide for their convenient guidance of their cannula into and within the right auricle, and their directing towards the various vena cavae in which they are to insert in preparation for the machine's operation. The orientation of the apertures 12 and 13 can be more clearly seen from FIGS. 2 through 5. In addition, the general cylindrical shape of the cylindrical means 7, in addition to its beaded mid-point 10, can be conveniently seen from these figures.

The dimensions of the introducer, for supporting the pair of cannulae, are of moderate dimensions, not being required to be more than approximately five centimeters in length. Each of the openings 12 and 13 provided through the confined end of the introducer are not necessarily greater than fifteen millimeters in diameter, and being approximately 90° apart. The tubular openings of the guide means, as at 8 and 9, upon the introducer means are somewhere in the vicinity of two centimeters in diametrical dimension.

In addition to the foregoing, the introducer means of this invention may be formed of a polymer, plastic, or even of rubber, and function adequately to properly receive the tying of the heart lining by means of a ligature therearound, during its maintenance through the heart wall, and which effectively reduces bleeding during performance of the surgical operation. Likewise, as previously explained, once the introducer means is removed, only a single row of sutures is required for sealing off the puncture or incision through the atrium lining, thus facilitating the rapid healing of the heart wall after surgery has been completed. Thus, the patient can be more quickly brought back into the mainstream of life, with the surgeon being more assured that the operation has been a success, and that post-healing of the patient will progress expeditiously and uneventfully due to only a single incision having been made through the heart lining.

It may also be commented that since the introducer means of this invention may be of a molded polymer, or related type of material, that its apertures 12 and 13 may also even be formed as slight length of tubular members, and which will be molded into directions that provide for the assured guidance of the various cannulae, during their introduction into the right auricle, specifically towards their various vena cava in which they are to locate in preparation for performance of this type of surgical operation.

Variations or modification to the invention may occur to those skilled in the art upon reviewing the subject matter of this disclosure. Such variations or modifications, if within the spirit of this invention, are intended to be encompassed within the scope of any claims to patent protection issuing hereon. The description of the invention set forth herein is done so for illustrative purposes only.

Having thus described the invention what is claimed and desired to be secured by Letters Patent is:

1. A cannula introducer for use during open heart surgery and related surgical operations, comprising, a cylindrical member, guide means integrally formed at one end of said cylindrical member and having dimensions of a size at least to accept the introduction of a pair of cannulae therein, said guide means comprising a pair of tubular-like members integrally formed with the cylindrical member, each said tubular-like member adapted for initially receiving one of the cannula therein during their introduction, the opposite end of the cylindrical member being formed into confinement, a pair of apertures formed through the confined end of the cylindrical member and capable of each receiving a cannula there through during their introduction and retention within the heart during surgery, said apertures provided through the confined end of the cylindrical member being angulated with respect to the longitudinal axis of the cylindrical member so that they are aligned and oriented towards the particular hearts arteries and veins for guiding the cannulae thereto and for their select insertion therein in preparation for a surgical operation.

2. The invention of claim 1 further comprising rim means formed proximate the mid-point of the introducer to facilitate the interim connection of the heart tissue therewith during a surgical operation.

3. The invention of claim 2 wherein said cannula introducer is formed from a polymer.

4. The invention of claim 2 wherein said cannula introducer is formed of rubber.

* * * * *